US007235588B2

(12) United States Patent
Siddiqui et al.

(10) Patent No.: US 7,235,588 B2
(45) Date of Patent: *Jun. 26, 2007

(54) METHOD FOR REDUCING HYPERTENSION AND HEART FAILURE

(75) Inventors: Mohammed A. Q. Siddiqui, Basking Ridge, NJ (US); Eduardo Mascareno, Brooklyn, NY (US); Daniel Lincoln Beckles, Carrollton, TX (US)

(73) Assignee: The Research Foundation of State University of New York, Albany, NY (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/488,279

(22) PCT Filed: Jul. 23, 2002

(86) PCT No.: PCT/US02/23444

§ 371 (c)(1),
(2), (4) Date: Jul. 14, 2004

(87) PCT Pub. No.: WO03/020202

PCT Pub. Date: Mar. 13, 2003

(65) Prior Publication Data

US 2004/0266661 A1     Dec. 30, 2004

Related U.S. Application Data

(63) Continuation-in-part of application No. 09/945,192, filed on Aug. 31, 2001, now Pat. No. 6,433,018.

(51) Int. Cl.
*A61K 31/165*     (2006.01)

(52) U.S. Cl. ...................................... 514/619

(58) Field of Classification Search ...................... None
See application file for complete search history.

(56) References Cited

U.S. PATENT DOCUMENTS

| 5,573,772 | A | 11/1996 | Downey et al. | |
|---|---|---|---|---|
| 6,255,296 | B1 | 7/2001 | Daniels | |
| 6,433,018 | B1 * | 8/2002 | Siddiqui et al. | ............ 514/619 |
| 2002/0028817 | A1 | 3/2002 | Levitzki et al. | |

FOREIGN PATENT DOCUMENTS

WO     98/06391     2/1998

OTHER PUBLICATIONS

Zarain-Herzberg, et al., Am. J. Cardiology, 1999;83:31H-37H.*
Alexander Levitzki, "Tyrphostins—Potential Antiproliferative Agents and Novel Molecular Tools," *Biochemical Pharmacology* (1990) 40/5: 913-918.
Shinji Negoro, Keita Kunisada, Erioh Tone, Masanobu Funamoto, Hidemasa Oh, Tadamitsu Kishimoto, Keiko Yamauchi-Takihara, "Activation of JAK/STAT pathway transduces cytoprotective signal in rat acute myocardial infarction," *Cardiovascular Research* (2000) 47: 797-805.
Alexander Levitzki and Aviv Gazit, "Tyrosine Kinase Inhibition: An Approach to Drug Development," *Science* (1995) 267: 1782-1788.
Eduardo Mascareno, Manya Dhar, and M.A.Q. Siddiqui, "Signal transduction and activator of transcription (STAT) protein-dependent activation of angiotensinogen promoter: A cellular signal for hypertrophy in cardiac muscle," *Proc. Natl. Acad. Sci. USA* (1998) 95: 5590-5594.
Naftaly Meydan, Tom Grunberger, Harjit Dadi, Michal Shahar, Enrico Arpaia, Zvi Lapidot, J. Steven Leeder, Melvin Freedman, Amos Cohen, Aviv Gazit, Alexander Levitzki and Chaim M. Roifman, "Inhibition of acute lymphoblastic leukaemia by a Jak-2 inhibitor," *Nature* (1996) 379: 645-648.
Alexander Levitzki, "Protein Tyrosine Kinase Inhibitors as Novel Therapeutic Agents," *Pharmacol. Ther.* (1999) 82/2-3: 231-239.
Eduardo Mascareno and M.A.Q. Siddiqui, "The role of Jak/STAT signaling in heart tissue renin-angiotensin system," *Molecular and Cellular Biochemistry* (2000) 212: 171-175.
Domenica Altavilla, Francesco Squadrito, Giuseppe M. Campo, Antonino Saitta, Giovanni Squadrito, Cristina Quartarone, Barbara Deodato, Mariarita Arlotta, Marcella Ferlito, Letteria Minutoli, Michelangelo Tringali, Giuseppe Urna, Aurora Sardella, Achille P. Caputi, "The reduction of myocardial damage and leukocyte polymorphonuclear accumulation following coronary artery occlusion by the tyrosine kinase inhibitor tyrphostin AG 556," *Life Sciences* (2000) 67: 2615-2629.
Stephanie W. Watts, Jennifer A. Florian and Kimberly M. Monroe, "Dissociation of Angiotensin II-Stimulated Activation of Mitogen-Activated Protein Kinase Kinase from Vascular Contraction," *The Journal of Pharmacology and Experimental Therapeutics* (1998) 286/3: 1431-1438.
Shao-Ling Zhang, Catherine To, Xing Chen, Janos G. Filep, Shiow-Shih Tang, Julie R. Ingelfiner, Serge Carrière, John S.D. Chan, "Effect of Renin-Angiotensin System Blockade on the Expression of the Angiotensinogen Gene and Induction of Hypertrophy in Rat Kidney Proximal Tubular Cells," *Experimental Nephrology* (2001) 9: 109-117.
Cindy Ruwhof, Arnoud van der Laarse, "Mechanical stress-induced cardiac hypertrophy: mechanisms and signal transduction pathways," *Cardiovascular Research* (2000) 47: 23-37.
Michael M. Givertz, MD, "Manipulation of the Renin-Angiotensin System," *Circulation* (2001) 104: e14-e18.
Diane H. Boschelli, "Small molecule inhibitors of receptor tyrosine kinases," www.prous.com/journals/dof/sample/html/df240515/df240515.html. *Date of publication unknown*.
Eduardo Mascareno, PhD; Mohammed El-Shafei, MD; Nilanjana Maulik, PhD; M.Sato, MD; Yueling Guo; Dipak Das, PhD; M.A.Q. Siddiqui, Phd, "JAK/STAT Signaling Is Associated With Cardiac Dysfunction During Ischemia and Reperfusion," *Circulation* (2001) 104:1-5.
DL Beckles, E. Mascareno, and MAQ Siddiqui, "Attenuation of Cardiac Hypertrophy in vivo by Interference with Activation of the Jak/Stat Pathway," presented at the *XVII World Congress of the International Society for Heart Research*, Winnipeg, Manitoba, Canada (Jul. 6-11, 2001).

* cited by examiner

*Primary Examiner*—Raymond J. Henley, III
(74) *Attorney, Agent, or Firm*—Hoffmann & Baron, LLP

(57) ABSTRACT

A method is provided for reducing hypertension and/or heart failure in a mammal. Preferably, the method is used to treat or prevent tissue damage to a human heart. The method includes administering an effective amount of a Jak2 inhibitor, preferably a tyrphostin, such as AG490.

17 Claims, 16 Drawing Sheets

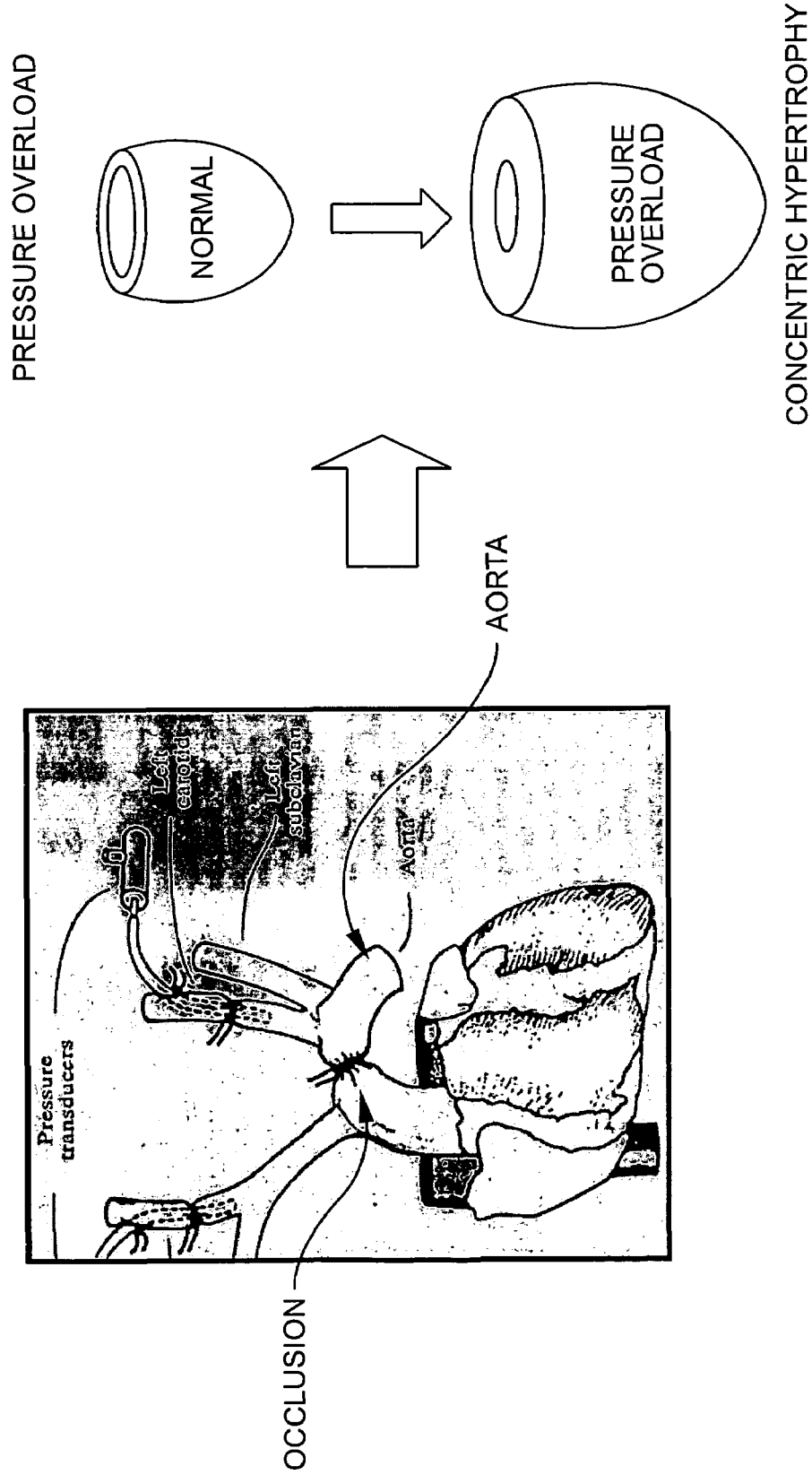
FIG. 1  TRANS AORTIC CONSTRICTION MODEL IN MICE.

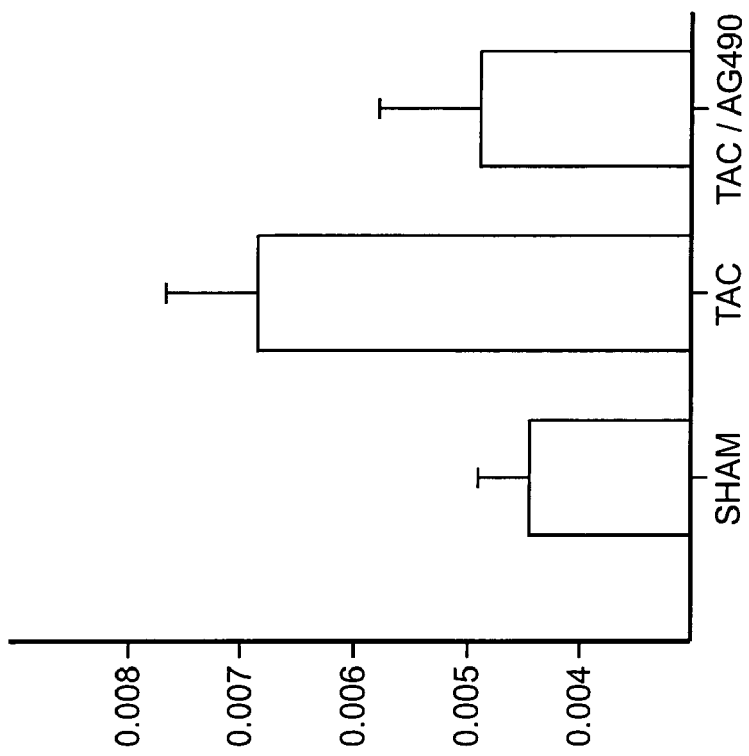
FIG. 2B  EFFECT OF AG490 ON CARDIAC HYPERTROPHY
- N = 5 IN EACH STUDY
- TAC/Ty IS THE ADMINISTRATION OF
- 5μM TYROPHOSTIN (AG490) i.p.
- DURATION 9 DAYS

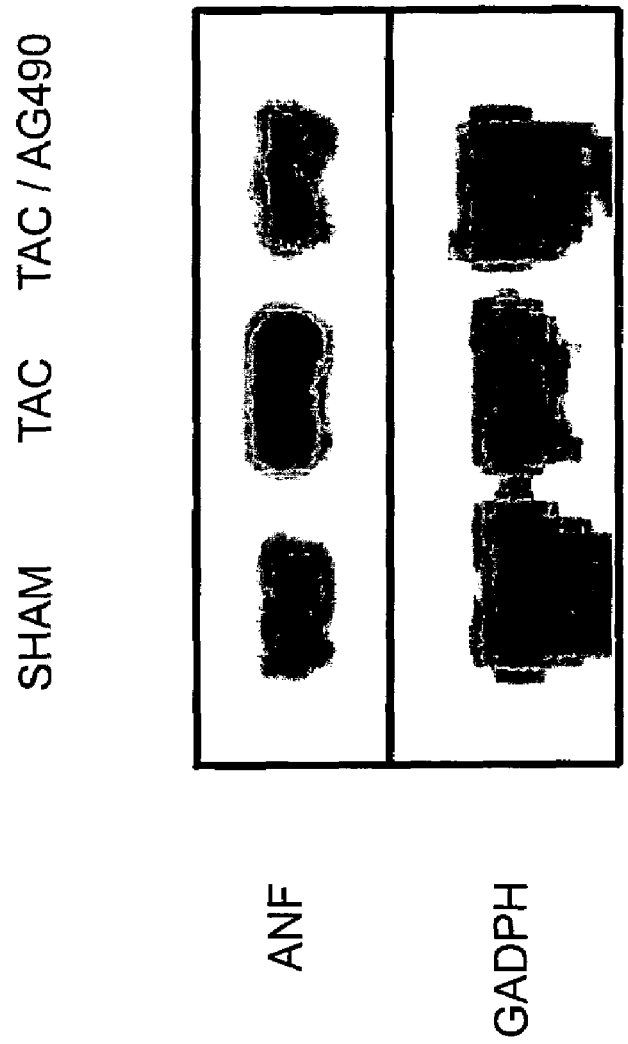
FIG. 3 CARDIAC HYPERTROPHY: NORTHERN BLOT

FIG. 6A

| STIMULUS | C | I/R | | |
|---|---|---|---|---|
| TYRPHOSTIN μM | - | - | 5 | 50 |
| JAK2 | | | | |

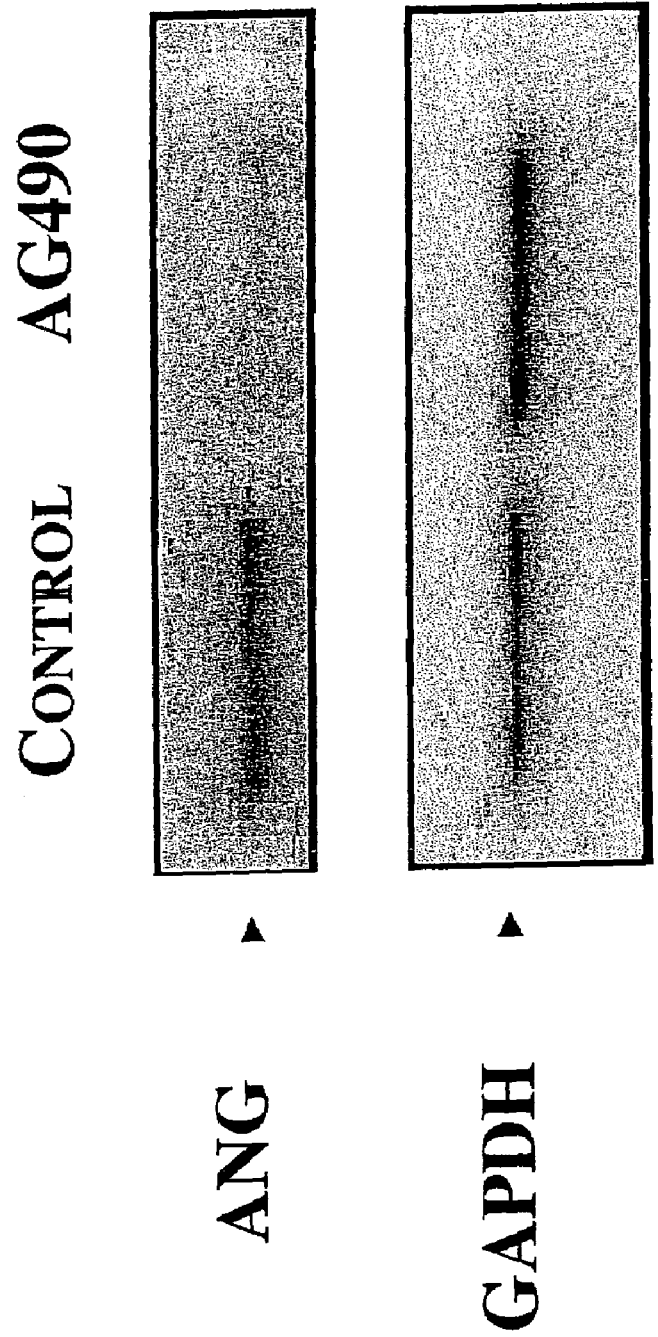
FIG. 8 AG490 effectively attenuates angiotensinogen mRNA expression in vivo

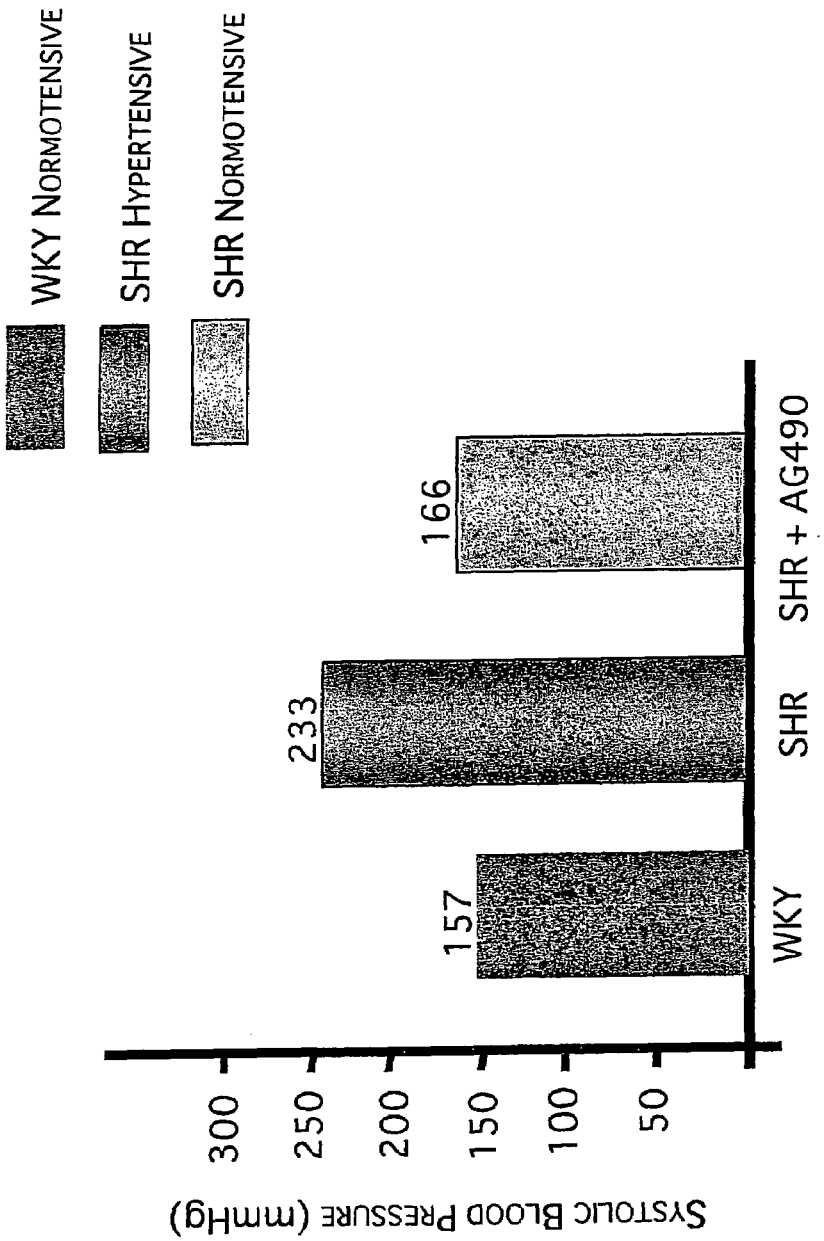
FIG. 9 CHRONIC TREATMENT WITH AG490 ATTENUATES HYPERTENSION IN SPONTANEOUSLY HYPERTENSIVE RATS

```
SEQUENCE LISTING

<160> NUMBER OF SEQ ID NOS: 3

<210> SEQ ID NO 1
<211> LENGTH: 24
<212> TYPE: DNA
<213> ORGANISM: Artificial
<220> FEATURE:
<223> OTHER INFORMATION: Primers

<400> SEQUENCE: 1
aggagatgaa aggggtggat gtat                                              24

<210> SEQ ID NO 2
<211> LENGTH: 15
<212> TYPE: DNA
<213> ORGANISM: Artificial
<220> FEATURE:
<223> OTHER INFORMATION: primers

<400> SEQUENCE: 2
gggttcctgg aaggg                                                        15

<210> SEQ ID NO 3
<211> LENGTH: 15
<212> TYPE: DNA
<213> ORGANISM: Artificial
<220> FEATURE:
<223> OTHER INFORMATION: primers

<400> SEQUENCE: 3
cccttccagg aaccc                                                        15
```

METHOD FOR REDUCING HYPERTENSION AND HEART FAILURE

This application is a continuation-in-part of U.S. Ser. No. 09/945,192 filed on Aug. 31, 2001, now U.S. Pat. No. 6,433,018, the entire specification is hereby incorporated by reference.

BACKGROUND OF THE INVENTION

This invention relates to methods for reducing hypertension, hypertrophy, ischemia, and/or heart failure.

Cardiovascular disease is the leading cause of death in the Western world, resulting in an estimated annual death toll of more than ten million people. Such diseases, such as chronic hypertension (high blood pressure), left ventricular hypertrophy (enlargement of the heart), and myocardial ischemia (cardiac cell injury) can culminate in heart failure.

The most prevalent cardiovascular disorder that contributes to heart failure is hypertension, which is a disease largely of the vasculature. The complex pathogenesis of hypertension is not fully understood, although it is believed that functional and/or structural changes in the blood vessels are the cause.

High blood pressure is a significant health problem for several reasons. First, only one-third of the patients receiving treatment have their illness under control. Furthermore, one-third of the population in the United States are estimated to have undetected hypertension (Kaplan, (1998) *Clinical Hypertension*. Baltimore: Williams & Williams).

The consequences of hypertension (e.g., hypertrophy, heart failure, coronary heart disease, aortic disease, and renal failure, etc.) are widespread and can be devastating. Victims can remain asymptomatic until much damage has already occurred. Furthermore, the detrimental effects of blood pressure increase continuously as the pressure increases.

As stated above, one consequence of hypertension is generally hypertrophy. Cardiac hypertrophy is an increase in the size of the heart. In humans, hypertrophy, is the compensatory response of the myocardium (cardiac muscle) to increased work as a result of an increase in blood pressure or blood volume (hemodynamic overload). The myocardium can increase in size but is not capable of increasing cell number.

Two patterns of hypertrophy can occur depending on the stimulus, either pressure-overloaded hypertrophy or volume-overloaded hypertrophy. Pressure-overloaded hypertrophy typically occurs as a result of hypertension. The ventricles develop concentric hypertrophy, and exhibit an increased ratio of wall thickness to cavity radius.

Volume-overloaded hypertrophy generally occurs as a result of a defect in one of the valves of the heart. The ventricles develop hypertrophy with dilatation (eccentric hypertrophy), resulting in a proportionate increase in ventricular radius and wall thickness.

Initially, the development of cardiac hypertrophy is advantageous since it results in the addition of sarcomeres (contractile units), thereby reducing ventricular wall stress to normal levels (Ruwhof et al., (2000) *Cardio. Res.*, 47:23-37). The increase in the number of sarcomeres leads to augmentation in the overall weight and size of the heart.

With prolonged hemodynamic overload, however, when the hypertrophied heart can no longer meet the increased demand in workload, the heart begins to dilate, stretching the sarcomeres and increasing the force of contraction and stroke volume. The increased stretching of the myocytes further perpetuates the hypertrophy.

Hypertrophy of the myocardium may become increasingly harmful due to the increased metabolic requirements of the enlarged heart. Molecular changes have been observed in the myocytes during development of myocardial hypertrophy. Such changes include the rapid induction of proto-oncogenes and heat shock protein genes, quantitative and qualitative changes in gene expression, and increased rate of protein synthesis (Ruwhof et al., (2000) *Cardio. Res.*, 47:23-37). Changes that occur in the hypertrophied heart may contribute to the development of heart failure. Moreover, ischemic heart disease and arrhythmias may develop, increasing the risk of death.

A different type of heart disease occurs as a result of ischemia. Ischemia is an imbalance between the supply and demand of the heart for oxygenated blood. In addition to insufficient oxygen, ischemia is also caused by a reduced availability of nutrient substrates and inadequate removal of metabolites. In the majority of cases, myocardial ischemia occurs as a result of the narrowing or obstruction of an artery due to atherosclerosis. Four ischemic syndromes may result depending on the rate of development and severity of the arterial narrowing and the myocardial response. The ischemic syndromes are angina pectoris, myocardial infarction, chronic ischemic heart disease, and sudden cardiac death.

The cardiac diseases described above can ultimately impair cardiac function and result in heart failure. Development of heart failure usually occurs slowly, often over many years. The heart gradually loses its ability to pump blood and therefore works less efficiently. As such, heart failure is typically defined as a clinical syndrome in which the heart is unable to maintain an output sufficient for the metabolic requirements of the tissues and organs of the body.

The tissue and systemic renin-angiotensin systems play a major role in regulation of pathological cardiovascular functions, such as in hypertension (Raizada et al., (1993) *Cellular and Molecular Biology of the Renin-Angiotensin System*, 515-555), left ventricular hypertrophy (Lavie et al., (1991) *Drugs* 42:945-946), ischemic dilated cardiomyopathy, and heart failure (Raynolds et al., (1993) *Lancet* 342: 1073-1075). The renin-angiotensin system also exists in other organs and tissues, including the heart, kidneys, prostate, brain, intestines, and the vasculature.

Normal homeostatic levels of a number of hemodynamic properties, such as blood pressure, blood volume, and vascular tone, are maintained by the renin-angiotensin system. Renin is an enzyme that was first isolated from the kidneys over a hundred years ago. Angiotensinogen is cleaved by renin to yield the inactive decapeptide angiotensin I. An enzyme is present in the vascular endothelium, especially in the lungs. The enzyme is angiotensin converting enzyme (ACE), which cleaves off two amino acids from angiotensin I to form the octapeptide, angiotensin II.

Angiotensin II is prominently involved in virtually all aspects of the renin-angiotensin activity. The angiotensin II then exerts its effects on target organs and tissues by binding its transmembrane domain G-protein coupled receptor ($AT_1$ and/or $AT_2$).

Binding of angiotensin II to its receptor can activate several different intracellular signal transduction pathways that use the well-known signal transducers, such as protein kinase A, protein kinase C, MAP kinase, and src (Sadoshima et al., (1993) *Circ. Res.* 73:413-423; Duff et al., (1995) *Cardiovasc. Res.* 30:511-517; Booz et al., (1995) *Cardiovasc. Res.* 30:537-543; Schieffer et al., (1996) *Hypertension* 27:476-480; Bernstein et al., (1996) *Trends Cardiovasc. Med.* 6:179-197).

In addition to these signal transduction pathways, angiotensin II also activates the Janus-associated kinase/signal transducer and activator of transcription (Jak/STAT) pathway. The components of the Jak/STAT pathway are present in a latent state in the cytoplasm of unstimulated cells. Binding of angiotensin II to its receptor leads to activation of Jak, a tyrosine kinase that phosphorylates STAT proteins and allows them to translocate to the nucleus. Within the nucleus, the phosphorylated STAT functions as a transcription factor (Ihle (1996) *Cell* 84:331-334) that recognizes and binds, in a sequence-specific fashion, to cis-regulatory elements in the promoter of target genes.

In mammals, the Jak family consists of Jak1, Jak2, Jak3, and Tyk2. Seven STAT proteins have been identified in mammalin cells, STAT1, STAT2, STAT3, STAT4, STAT5A, STAT5B, and STAT6.

Jaks are crucial components of diverse signal transduction pathways that govern important cellular functions, including cell survival, proliferation, differentiation and apoptosis. Interfering with Jak activity may lead to the loss of a vital signal transduction pathway, thereby disrupting normal cellular processes needed for cell survival. Therefore, it is important to selectively inhibit particular Jaks that are involved in various disease states. For example, Jak2 has been suggested to be involved in the upregulation of angiotensinogen promoter activity in hypertrophy and ischemia (Mascareno E, et al. (2000) *Mol. Cell. Biochem.* 212:171; and Mascareno E, et al (2001) *Circulation* 104:1).

Inhibitors of Jaks include tyrphostins, which are a class of compounds that inhibit protein tyrosine kinases. The tyrosine kinases that are inhibited depends on the substituents that are present on the tyrphostin.

One particular tyrphostin, AG490, selectively inhibits Jak2 and has been proposed for treating cancer (Meydan N, et al. (1996) *Nature* 379:645). Administration of tyrphostin AG490 has been suggested to afford cardioprotection to hearts subjected to ischemia/reperfusion (Mascareno E, et al. (2000) *Mol. Cell. Biochem.* 212:171 and Mascareno E, et al (2001) *Circulation* 104:1). However, the reference does not disclose treating hypertension and/or heart failure with tyrphostin AG490.

Tyrphostin AG556 is a protein tyrosine kinase inhibitor that reduces myocardial damage due to ischemia (Altavilla D., et al, (2000) *Life Sciences* 67:2615). There is no indication that tyrphostin AG556 is a selective Jak2 inhibitor. The lack of selectively is a problem since it can lead to side effects.

There has been an ongoing search for effective long-term treatments for myocardial dysfunction. Currently, treatments include administering drugs, such as vasiodilators, beta-blockers, free-radical scavengers, and calcium antagonists. Another type of treatment is surgery and includes by-pass surgery and angioplasty. Virtually all of these methods have been ineffective for favorable long-term results.

Heart muscle cannot currently be regenerated. As a consequence, affected individuals must contend with damaged heart tissue for the rest of their lives. Therefore, restoring normal cardiac function to heart muscles damaged by cardiovascular disease has been a long-term goal of cardiology.

Therefore, there is an immediate need for therapeutic agents that prevent and/or reverse the damage caused by myocardial dysfunction without harming healthy cells.

SUMMARY OF THE INVENTION

These and other objectives have been met by providing a method for reducing hypertension in a mammal at risk for said hypertension. The method comprises administering to said mammal an effective amount of a selective Jak2 inhibitor.

In another embodiment, the invention provides a method for reducing hypertrophy of an organ in a mammal at risk for said hypertrophy. The method comprises administering to said mammal an effective amount of a pharmaceutical composition comprising a selective Jak2 inhibitor.

In yet another embodiment, the invention relates to a method for reducing ischemia of an organ in a mammal at risk for said ischemia. The method comprises administering to said mammal an effective amount of a pharmaceutical composition comprising a selective Jak2 inhibitor.

In a further embodiment, the invention relates to a method for reducing heart failure in a mammal at risk for said heart failure. The method comprises administering to said mammal an effective amount of a selective Jak2 inhibitor.

BRIEF DESCRIPTION OF THE DRAWINGS

FIG. 1: depicts a model for transverse aortic constriction (TAC) in mice.

FIG. 3: depicts ANF inhibition by tyrphostin AG490 during cardiac hypertrophy.

FIG. 6A: depicts Jak2 inhibition by tyrophostin AG490 during ischemia/reperfusion (I/R).

FIG. 8: depicts attenuation of angiotensinogen mRNA expression in vivo by tyrphostin AG490.

FIG. 9: depicts attenuation of hypertension by tyrphostin AG490 in spontaneously hypertensive rats.

DETAILED DESCRIPTION OF THE INVENTION

Figure 2A:
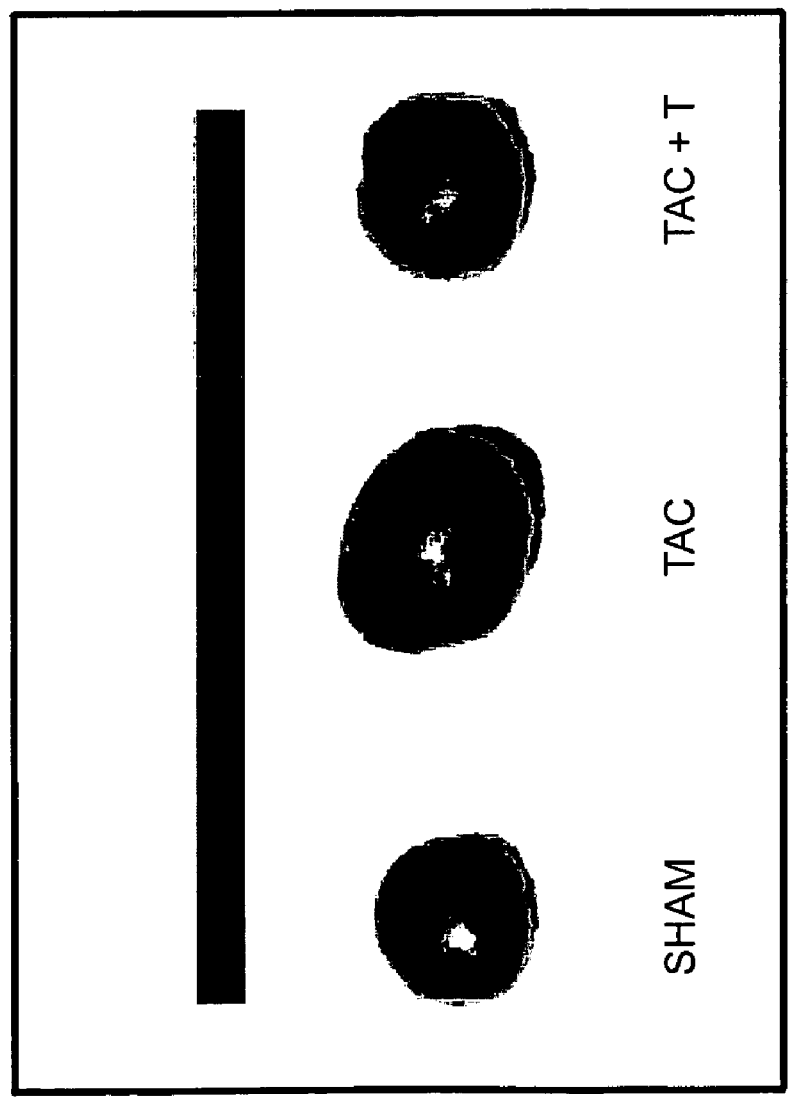
FIG. 2: depicts cardioprotection of left ventricular hypertrophy (LVH) by tyrphostin AG490. A) Visual inspection of cross section of the heart demonstrates a decrease in LVH in tyrphostin AG490 treated animals. B) Histogram demonstrates a decrease in ratio of heart weight to body weight in tyrphostin AG490 treated animals. C) Light microscopy of cardiomyocytes of left ventricle demonstrates a decrease in hypertrophy in tyrphostin AG490 treated animals.

The present invention is based on the discovery by the inventors that a specific signaling pathway is responsible for the onset and maintenance of the renin-angiotensin system in hypertension, hypertrophy, and ischemia. The inventors have discovered that the activation of Jak2, during hypertension, hypertrophy and ischemia activates specific STAT proteins, specifically STAT 3, STAT5A and STAT6. Moreover, the inventors have discovered that administration of a Jak2 inhibitor significantly reduces hypertension, and myocardial damage caused by hypertrophy and ischemia Administration of a Jak2 inhibitor can also significantly reduce heart failure.

Hypertension

In one embodiment, the invention provides a method for reducing hypertension in a mammal at risk for hypertension. The method comprises administering to said mammal an effective amount of a selective Jak2 inhibitor.

Hypertension is typically a disease of the vasculature that causes high blood pressure. High blood pressure usually occurs as a result of resistance in the blood vessels to blood flow. The resistance may, for example, be due to functional or structural changes to the blood vessels (e.g., artheroscle-rosis, arteriolosclerosis, and arteriolitis). The greater the resistance to blood flow, the harder the heart must work to maintain an adequate blood flow to the body, thus resulting in a higher blood pressure.

Hypertension can be defined by an elevated diastolic and/or systolic blood pressure. The healthy (e.g., normal) and elevated diastolic and/or systolic blood pressure for a particular mammal is known to those skilled in the art.

For example, in humans, high blood pressure is typically defined when the sustained diastolic pressure is greater than about 85 mm Hg, in more serious cases greater than about 100 mm Hg, and in the most serious cases greater than about 115 mm Hg. Using systolic pressure as a measurement, in humans, high blood pressure is typically defined when the sustained systolic pressure is greater than about 140 mm Hg, in more serious cases greater than about 150 mm Hg, and in the most serious cases greater than about 160 mm Hg.

Hypertension may be assessed by any method known to those skilled in the art. For example, blood pressure may be measured with a blood pressure cuff and gauge or with a blood pressure monitor (e.g., electronic sphygmomanometer).

Hypertrophy

In another embodiment, the invention relates to a method for reducing hypertrophy of an organ in a mammal at risk for hypertrophy. The method comprises administering to said mammal an effective amount of a pharmaceutical composition comprising a selective Jak2 inhibitor.

Hypertrophy is the enlarging of an organ. The increase in size may, for example, be due to an increase in workload due to some physical defect in the organ itself or one of the biological systems supporting the organ.

Several organs are subject to hypertrophy. Some examples include the heart, kidney, and prostate.

Myocardial hypertrophy, for example, is hypertrophy of the heart, which is typically caused by either myocardial valve damage or high blood pressure. Myocardial hypertrophy may also result from a dilation or expansion of the heart in response to heart muscle damage that causes weak muscle action. Hypertrophic damage may lead, for example, to myocardial infarction, congestive heart failure, and cardiomyopathy.

Left ventricular hypertrophy (LVH) is the medical term for enlargement of the left ventricle of the heart. The left ventricle is the heart's main pumping chamber, and pumps oxygenated blood via the aorta through the systemic circulation.

Hypertrophy may be assessed, for example, by any method known to those skilled in the art. For example, the weight of the organ relative to the body weight of the mammal may be expressed as a ratio, as described in Example 1 and depicted in FIG. 2B.

Ischemia

In a further embodiment, the invention relates to a method for reducing ischemia of an organ in a mammal at risk for ischemia. The method comprises administering to said mammal an effective amount of a pharmaceutical composition comprising a selective Jak2 inhibitor.

Ischemia is a deficiency of oxygenated blood. The deficiency of blood may, for example, be caused by functional constriction or obstruction of a blood vessel. The lack of oxygen and/or reduced availability of nutrient substrates and inadequate removal of metabolites may result in tissue damage, for example, apoptosis and/or necrosis of cells.

Several organs are subject to ischemia. Some examples include, but are not limited to, the heart, brain, kidney, and intestines.

Ischemic heart disease is often caused by a reduction in coronary blood flow relative to myocardial demand. The reduction in blood flow may result from a variety of reasons, and typically occurs as a result of atherosclerosis.

As a result of ischemic damage to the heart muscle, the damaged area ceases to contract. Symptoms of such damage include, but are not limited to, cardiac arrhythmias, angina, myocardial infarction, congestive heart failure, and sudden cardiac death.

Ischemia may be assessed by any method known to those skilled in the art. An assessment of ischemic damage may be made, for example, by measuring the infarct (scar) size of the organ, as described in Example 2 and depicted in FIG. 4B.

Heart Failure

In yet another embodiment, the invention relates to a method for reducing heart failure in a mammal at risk for heart failure. The method comprises administering to said mammal an effective amount of a selective Jak2 inhibitor.

Heart failure is a clinical syndrome resulting from disturbances in cardiac output or from increased venous pressure. The disturbances in cardiac output or increased venous pressure can be due to dilated cardiomyopathy, myocardial fibrosis, deposition of amyloid, constrictive pericarditis, hypertension, hypertrophy and/or ischemia.

Injury to the heart muscle by hypertension, hypertrophy and/or ischemia often decreases the ability of the heart to contract. Therefore, the heart cannot pump with ample force to push a sufficient amount of blood into the circulation.

In addition, injury to the heart muscle can prevent the heart from fully relaxing. As a consequence, the heart cannot properly fill with blood.

Heart failure may be assessed by any method known to those skilled in the art. An assessment of heart failure may be made, for example, by the symptoms associated with heart failure, such as chest pain, shortness of breath, excess fluid in the lungs, fatigue, and/or swollen ankles and feet.

Instruments can be used to quantitate the symptoms of heart failure and are known to those skilled in the art. For example, a caliper can be used to measure the amount of swelling in the ankles and feet and a spirometer can be used to measure lung capacity to determine shortness of breath.

An assessment of heart failure can also be made by measuring heart function. Instruments used to evaluate heart function include an electrocardiogram (i.e., measures electrical activity of a heartbeat) or echocardiography (measures abnormal heart size, shape, movement and/or amount of blood pumped out of the heart when the heart contracts).

Effects of Treatment

The methods of the invention result in inhibition of Jak2, thereby reducing hypertension, hypertrophy, ischemia, and/or heart failure.

Reducing hypertension means a significant reduction in the elevated blood pressure of a mammal relative to a healthy blood pressure. Hypertension is considered significantly reduced if the elevated diastolic and/or systolic pressure is reduced by at least about 10%, preferably at least about 25%, more preferably at least about 50%, even more preferably at least about 75%, and most preferably about 100% (e.g., bringing the pressure down to normal levels).

Reducing hypertrophy of an organ means a significant reduction in the size of a hypertrophic organ relative to a healthy organ. Reducing ischemia of an organ means a significant reduction in the infarct size of an ischemic organ. Hypertrophy or ischemia is considered significantly reduced if the size of the hypertrophic organ or the infarct size of the ischemic organ is reduced by at least about 10%, preferably at least about 25%, more preferably at least about 50%, even more preferably at least about 75%, and most preferably about 100%.

Reducing heart failure means a significant reduction in the symptoms of heart failure or heart function relative to a healthy heart. Heart failure is considered significantly reduced if the symptoms of heart failure or heart function is reduced by at least 10%, preferably at least about 25%, more preferably at least about 50%, even more preferably at least about 75%, and most preferably about 100%.

Any mammal may be treated in accordance with the invention. Mammals include, for example, humans, baboons and other primates, as well as pet animals such as dogs and cats, laboratory animals such as rats and mice, and farm animals such as horses, sheep, and cows.

A mammal at risk for hypertension, hypertrophy, ischemia, and/or heart failure may be susceptible for any number or reasons, including a genetic predisposition and/or environmental insult. Some examples of reasons for susceptibility to hypertension include, but are not limited to, familial history of high blood pressure, atherosclerosis, arteriolosclerosis, arteriolitis, diet and lifestyle, and side effects of medication. Some examples of reasons for susceptibility to hypertrophy include, but are not limited to, familial history of high blood pressure, valvular heart disease, and side effects of medication. Valvular heart disease includes, for example, congenital heart disease and rheumatic heart disease. Some examples of reasons for susceptibility to ischemia include, but are not limited to, familial history of atherosclerosis, diet and lifestyle, surgical procedures, and side effects of medication. Some example of reasons for susceptibility to heart failure include, but are not limited to, dilated cardiomyopathy, myocardial fibrosis, deposition of amyloid, constrictive pericarditis, hypertension, hypertrophy and ischemia.

Jak2 Inhibitors

A Jak2 inhibitor is any compound that selectively inhibits the phosphorylation of the Jak2 protein in the Jak/STAT pathway. The compound may directly inhibit Jak2, or a component upstream of Jak2. The inhibition of the Jak2 protein must be sufficient to substantially inhibit and preferably prevent the Jak/STAT cascade.

The Jak2 inhibitor may be any type of compound. For example, the compound may be a small organic molecule or a biological compound, such as an antibody or an enzyme.

Examples of Jak2 inhibitors include some members of a class of small organic molecules called tyrphostins. Tyrphostins inhibit the activity of protein tyrosine kinases and have the basic structure shown in structure 1 below:

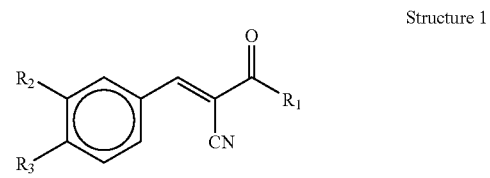

Structure 1

More than one hundred tyrphostins have been synthesized.

The tyrphostin may be any tyrphostin that selectively inhibits Jak2. Some examples of tyrphostins include the various structures described in Meydan et al., (1996) *Nature*, 379:645-648; Levitzki et al, (1995) *Science*, 267:1782-1788; and PCT application WO 98/06391. These structures are incorporated herein by reference.

A preferred class of tyrphostins for use are those compounds represented by structure 1 wherein:

$R_1 = C_6H_5 - CH_2 - NH$;

$R_2$ and $R_3 =$ H, OH, lower alkyl, F, $NO_2$, $CF_3$, $C_6H_5 - SO_2$, $O - R_4$, $O - CO - R_4$, or $R_4$ $R_4 =$ phenyl or lower alkyl; and lower alkyl = $C_1$-$C_4$ branched or unbranched alkyl (for example, methyl or ethyl).

$R_2$ and $R_3$ may be the same or different except $R_2$ and $R_3$ cannot both be H. Preferably, $R_2$ and $R_3$ are OH. The preferred compound has $R_1 = C_6H_5 - CH_2 - NH$, $R_2 = OH$, and $R_3 = OH$. The preferred compound is known as Tyrphostin AG490, which is a selective, specific, and potent Jak2 protein tyrosine kinase inhibitor. The structure of AG490 is shown as structure 2 below:

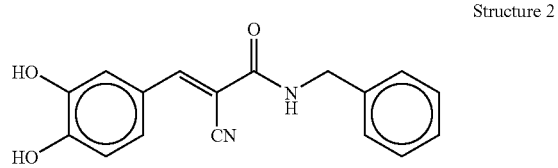

Structure 2

The tyrphostins may be made by methods known in the art, for example, as described in the PCT application WO 98/06391. Briefly, the typhostins may be synthesized by Knoevenagel condensation of the appropriate benzaldehyde with malononitrile, the appropriate substituted amide, or other appropriate Knoevenagel condensation partner.

A compound is considered a selective inhibitor of Jak2 when the compound inhibits Jak2 activity to an extent significantly greater than it inhibits the activity of other members of the Jak family, e.g., Jak1, Jak3, and Tyk2.

Preferably, the selective inhibitor inhibits Jak2 at least 2-fold more than it inhibits other members of the Jak family, more preferably at least about 5-fold more, and most preferably at least about 10-fold more.

Methods for screening for compounds that inhibit members of the Jak family are known in the art. For example, a phosphotyrosine assay is described in Example 5 and depicted in FIG. 6A. See also *Molecular Cloning A Laboratory Manual* by J. Sambrook and D. W. Russel, 2001.

Jak2 inhibitors as defined herein also include pharmaceutically acceptable salts. As used herein, pharmaceutically acceptable salts may be formed by treating the compounds identified above with salt-forming acids and bases which do not substantially increase the toxicity of the compound.

Compositions

In a preferred embodiment, the Jak2 inhibitor is administered in a pharmaceutical composition. The pharmaceutical composition may be manufactured by known means. The pharmaceutical compositions are preferably sterile, non-pyrogenic and isotonic preparations, optionally with one or more of the pharmaceutically acceptable additives listed below.

The pharmaceutical composition may be any composition suitable for pharmaceutical use in a mammal, especially a human. The composition may, for example, be in the form of a solid, a solution, or a suspension.

Pharmaceutical compositions of the Jak2 inhibitors of the invention are preferably stable compositions which may comprise one or more of the following: a stabilizer, a surfactant, preferably a nonionic surfactant, and optionally a salt and/or a buffering agent. The pharmaceutical composition may be in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% by weight of the Jak2 inhibitor.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolarity at a level suitable for administration to a human or an animal. Preferably, the salt or buffering agent is present at a roughly isotonic concentration of about 150 mM to about 300 mM.

The pharmaceutical compositions of the present invention may additionally contain one or more conventional additive. Some examples of such additives include a solubilizer such as for example, glycerol; an antioxidant such as, for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

An effective amount of a Jak2 inhibitor is the amount which reduces hypertension, hypertrophy, ischemia, and/or heart failure. Optimal doses can be determined by those skilled in the art based on a number of parameters including, for example, age, sex, weight, severity of the condition being treated, the compound being administered, and the route of administration. For example, an effective amount of Jak2 inhibitor can be that amount that would produce a blood serum concentration (volume level) of between about 0.01 µM to about 50 µM, preferably between about 0.05 to 10 µM, and more preferably between about 1.0 µM to about 5 µM.

Administration

The Jak2 inhibitor can be administered by any suitable method, as is known in the art. For example, the Jak2 inhibitor can be administered topically or systemically. Systemic administration is preferred. Administration using controlled release delivery systems, as is known in the art, is also contemplated herein.

Systemic administration includes both parenteral and enteral routes. For example, Jak2 inhibitors such as tyrphostins can easily be administered intravenously, which is a preferred route of delivery. Intravenous administration can be accomplished by mixing the Jak2 inhibitor in a suitable pharmaceutical carrier (vehicle) or excipient as understood by practitioners in the art.

Oral or enteral administration includes, for example, formulations such as tablets, capsules, pills, troches, elixirs, suspensions, syrups, wafers, chewing gum and the like.

The Jak2 inhibitor may be administered as a protective agent before hypertension, hypertrophy, ischemia, and/or heart failure occurs. For example, the Jak2 inhibitor may be used as a prophylactic treatment to prevent hypertension, hypertrophy, ischemia, and/or heart failure in a mammal at risk for hypertension, hypertrophy, ischemia, and/or heart failure. To prevent heart failure, for example, the Jak2 inhibitor may be administered to a mammal suffering from hypertension.

In another embodiment, the Jak2 inhibitor may be administered after the hypertension, hypertrophy, ischemia, and/or heart failure occurs in order to minimize and/or reverse, as well as to prevent, further damage resulting from hypertension, hypertrophy, ischemia, and/or heart failure. When administering the Jak2 inhibitor after hypertension, hypertrophy, ischemia, and/or heart failure has occurred, it is preferred that the Jak2 inhibitor be administered as soon thereafter as possible. It is particularly preferred to administer a Jak2 inhibitor before hypertension occurs to prevent any damage. Jak2 can also be administered while the hypertension, hypertrophy, ischemia, and/or heart failure is occurring.

Without being bound by theory, it is believed that the methods of the invention described can inhibit the activation of Jak2 and therefore interfere with the maintenance of the autocrine loop of the renin-angiotensin system, thereby acting as a protective agent.

EXAMPLE 1

This example demonstrates cardioprotection from left ventricular hypertrophy by Tyrphostin AG 490.

Pressure overload was produced by transverse aortic constriction (TAC) to induce left ventricular hypertrophy (FIG. 1). Briefly, male C57/BL6 mice, weighing 20 to 24 grams, were anesthetized by intra-peritoneal injection of a cocktail of ketamine (100 mg/kg) and xylazine (5 mg/ml).

The mice were shaved, restrained, and orally intubated (under direct vision via a vertical cervical incision) using a 22 guage blunt feeding needle. Respiration was artificially controlled (tidal volume of 0.1 to 0.3 ml) at a respiratory rate of 110 to 150 breaths/minute using a ventilator (Harvard Apparatus Rodent Ventilator, model 683). A median sternotomy was performed and the sternum retracted. The thymus was retracted anteriorly and the aortic arch identified and ligated (using 8.0 nylon suture; Ethicon) between the innominate and left common carotid artery with an overlying 27-guage needle; and then the needle removed to leave a discrete region of stenosis. The chest was then closed in two layers (using 6.0 vicryl suture, Ethicon) and the pneumothorax evacuated. Some mice were subjected to a sham operation in which the aortic arch was visualized but not banded. The mice were then extubated and monitored post-op for 3 to 12 hours. The survival rate at the end of the learning period is greater than 90%.

Figure 2C:
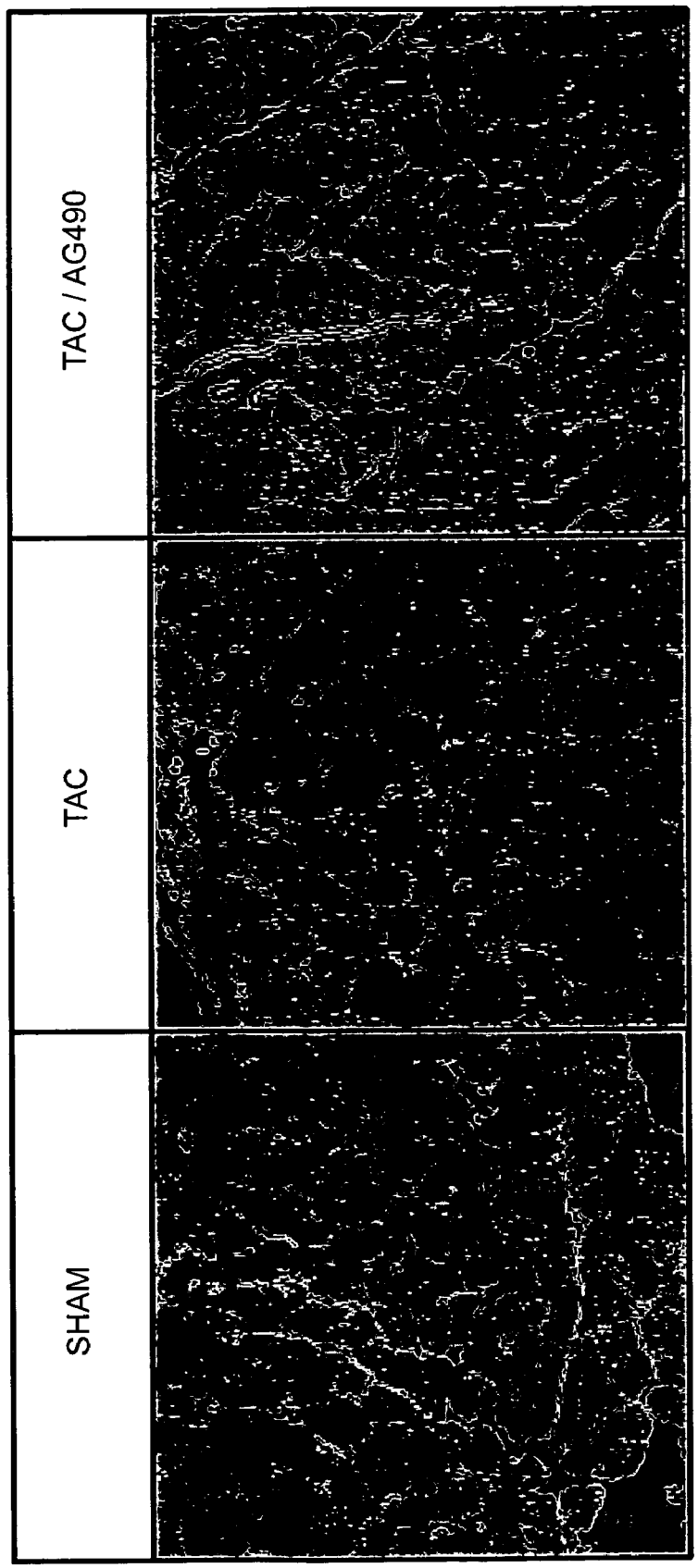

Nine days post-op, the hearts were removed from heparinized (500 U) mice and euthanized with a lethal dose of pentobarbital (150 mg/kg). The hearts were analyzed by visual inspection of a cross-section of the heart (FIG. 2A), determination of heart to body weight ratio (FIG. 2B), and light microscopy of the cardiomyocytes in the left ventricular (FIG. 2C), and activation of artiel natuiretic factor (ANF), a specific molecular marker for hypertrophy (FIG. 3). Based on these determinations, all trans-aortic constricted mice developed well-defined left ventricular hypertrophy.

To determine whether tyrphostin AG490 could reverse the hypertrophy induced by traverse aortic constriction, tyrphostin AG490 (5 µM) was administered to the mice, intraperitoneal, 24 hours before being subjected to transverse aortic constriction and every 24 hours thereafter for the duration of the study (9 days). Chronic administration of tyrophostin AG490 caused a remarkable reversal of hypertrophy (see FIGS. 2A, 2B, 2C, and 3).

EXAMPLE 2

This example demonstrates that administration of Jak2 afforded cardioprotection against ischemia-induced changes in myocardial performance by inhibition of Jak2.

Figure 4A:
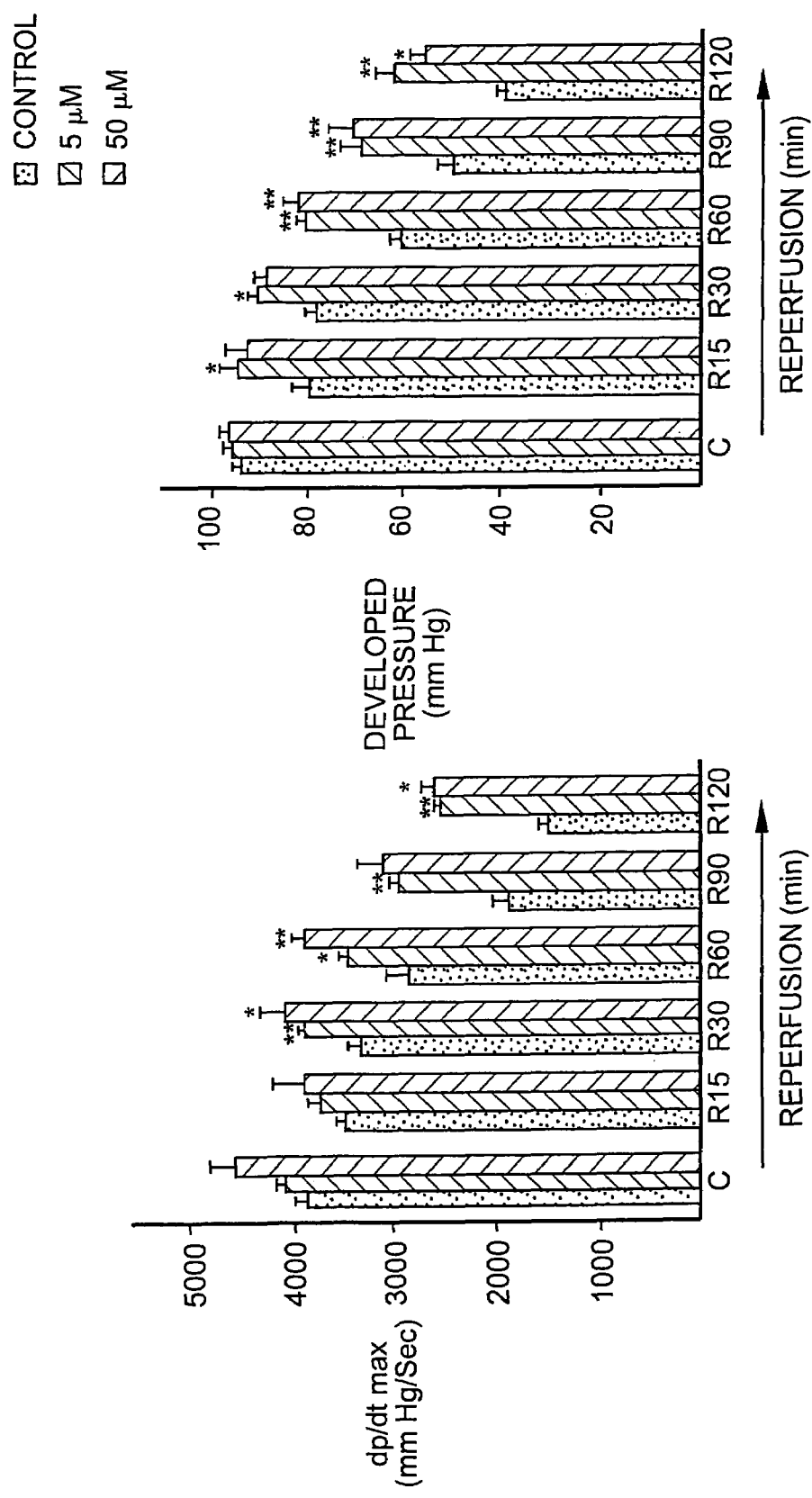
FIG. 4A: depicts the effects of tyrphostin AG490 on myocardial function.
Figure 4B:
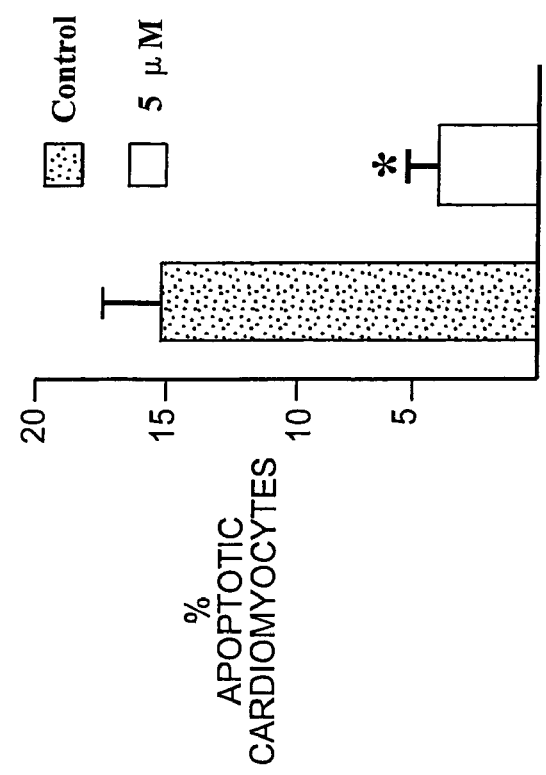
FIG. 4B: depicts reduction of infarct size by tyrphostin AG490 during ischemia/reperfusion.

Using spontaneously beating working hearts that were not paced, the absolute values and the first derivative of developed pressure were progressively decreased with reperfusion, as expected (FIG. 4A). The inhibitor, tyrphostin AG490, at both 5 and 50 µmol/L, was able to provide cardioprotection to approximately the same degree. This was particularly true during the first 60 min. of reperfusion, when the dP/dt value was not lowered, and developed pressure was minimally lowered, in the treated groups. The baseline value for dP/dt increased slightly in high (50 µmol/L) concentrations of tyrphostin AG490. In addition, the slopes of the decay for the treated and untreated groups after 60 min. were similar. The values for both dP/dt and developed pressure in all treated groups were significantly higher than in the untreated group. Developed pressure was notably higher in the tyrphostin groups subjected to 60 min. of reperfusion, R-60 (86±2.5 and 86±4.8 compared with 64±3.2 mm Hg); 90 min. of reperfusion, R-90 (69±5 and 72.7±5.7 compared with 46±3 mm HG); and 120 min. of reperfusion, R-120 (60.85±4 and 53.75±7 compared with 38.66±2 mm Hg). dp/dt values were markedly higher in groups at both concentrations throughout most of the reperfusion period compared with the control reperfused group, the difference being apparent at R-30 (3818±49.46 and 4156±238 versus 3382±68.8), R-60 (3362±53.14 and 3840±140 versus 2878±237), R-90 (2840±88 and 3194.7±228 versus 1842±162), and R-120 (2552±58.9 and 2626±269 versus 1543±94).

To gain insight into the physiological basis for cardioprotection afforded by tyrphostin AG490, the extent of cardiomyocyte infarct size and apoptosis were measured. On termination of treatment with tyrphostin AG490, hearts were immersed in 1% triphenyl tetrazolium solution in phosphate buffer ($Na_2HPO_4$ 88 mmol/l, $NaH_2PO_4$ 1.8 mmol/l) for 10 min. at 37° C. and stored at −70° C. for processing. Frozen hearts (ventricular tissue) were sliced transversely in a plane perpendicular to the apicobasal axis into 0.5 mm thick sections, blotted dry, placed between microscope slides, and scanned on a Hewlett-Packard Scanjet 5 p single-pass flat-bed scanner. With the NIH 1.61 image processing software, each digitized image was subjected to equivalent degrees of background subtraction, brightness, and contrast enhancement for improved clarity and distinctness. Risk (equivalent to total left ventricular muscle mass) and infarct zones of each slice were traced, and the respective areas were calculated in terms of pixels. The weight of each slice was then recorded to facilitate the expression of total and infarct masses of each slice in grams. The risk and infarct volumes of each slice in cubic centimeters were then calculated on the basis of slice weight to correct for any errors due to nonuniformity of heart slice thickness. The risk volumes and infarct volumes of each slice were summed to obtain the risk and infarct volumes for the whole heart. Infarct size was taken to be the percent infarct volume/risk volume for any one heart.

Immunohistochemical detection of apoptotic cells was carried out by use of terminal dUTP nick end-labeling (TUNEL), in which residues of digoxigenin-labeled dUTP are catalytically incorporated into the DNA by terminal deoxynucleotidyl transferase II. The cells were incubated with a sheep polyclonal anti-digoxigenin antibody followed by a FITC-conjugated rabbit anti-sheep IgG as a secondary antibody. The heart sections were washed in PBS 3 times, blocked with normal rabbit serum, and incubated with mouse monoclonal antibody recognizing cardiac myosin heavy chain (Biogenesis Ltd) followed by staining with TRIRC-conjugated rabbit anti-mouse IgG (200:1 dilution, Dalco, Japan). The fluorescence staining was viewed with a confocal laser microscope (Olympus Co). The apoptoic cells were counted and expressed as percentage of total myocyte population.

Figure 4C:
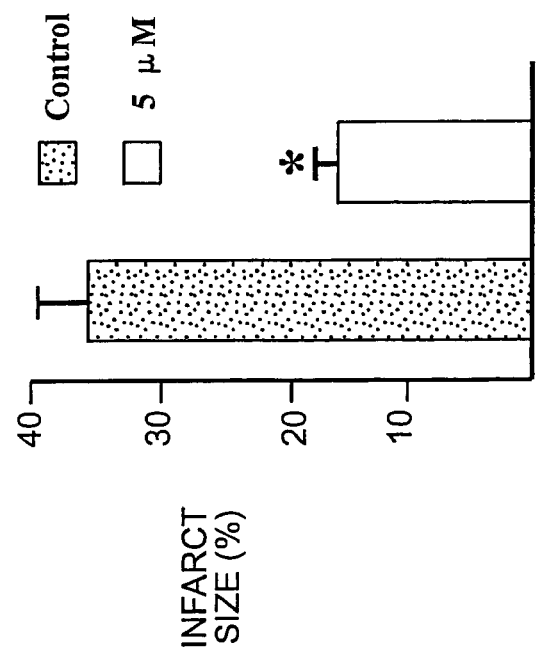
FIG. 4C: depicts reduction of apoptosis of cardiomyocytes by tyrphostin AG490 during ischemia/reperfusion.

Administration of tyrphostin AG490 reduced myocardial infarct size (FIG. 4B) and caused a marked lowering of apoptotic cell death (FIG. 4C), thereby, attributing, at least in part, to the recovery of contractile function upon treatment with tyrphostin AG490.

EXAMPLE 3

This example demonstrates upregulation of rat heart angiotensinogen mRNA during ischemia/reperfusion.

Ischemia was induced by a modified Langendorf-reperfusion method in rat hearts. Hearts from adult male rats were randomly divided into 4 groups and subjected to ischemia/reperfusion. In the ischemic group, hearts were perfused with Krebs-Henseleit buffer for 60 minutes, followed by 30 minutes of global ischemia. In the ischemic/reperfused group, hearts were perfused for 60 minutes, followed by 30 minutes of global ischemia and 120 minutes of reperfusion. Control group hearts were perfused for the same lengths of time.

Figure 5A:
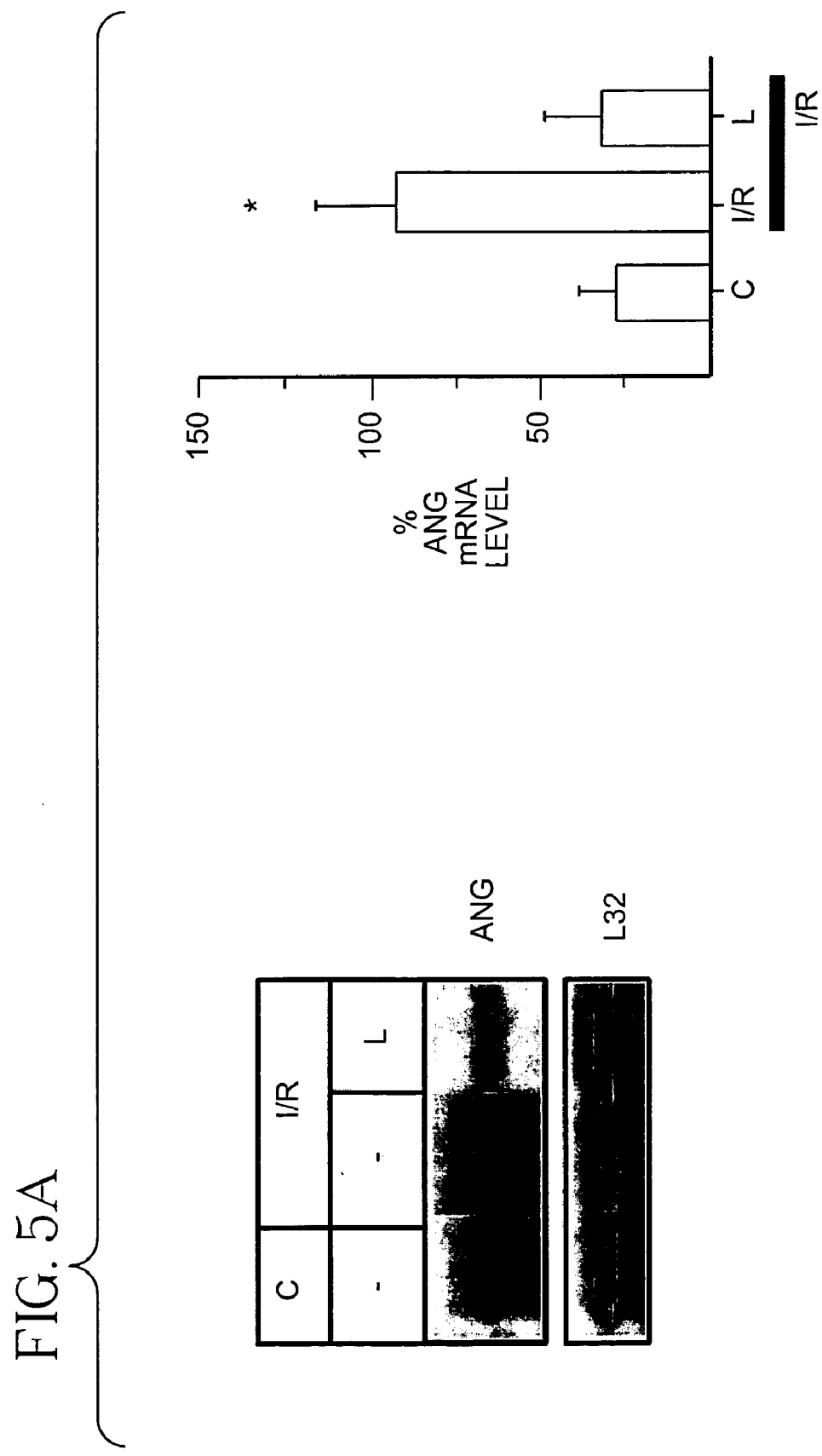
FIG. 5: depicts up-regulation of angiotensinogen mRNA during ischemia/reperfusion (I/R) is mediated by STATs. A) Angiotensinogen mRNA is increased during ischemia/reperfusion. B) St-domain/STAT binding activity is increased in hearts subjected to ischemia/reperfusion. C) STAT5A and STAT6 are activated in ischemic hearts.

Rat hearts subjected to ischemia/reperfusion were tested to determine whether activation of the renin-angiotensin system, as reflected by an increase in angiotensinogen mRNA, occurs in ischemic injury. The level of angiotensinogen mRNA was analyzed by primer extension assay using gene-specific DNA probes. A DNA primer spanning the complementary sequence of the rat angiotensinogen cDNA between nucleotides 302 and 279 (5'-AGGAGAT-GAAAGGGGTGGATGTAT-3') SEQ ID NO: 1 was end-labeled and used to evaluate the expression of angiotensinogen mRNA in total RNA isolated from the rat heart. The primer extension protocol was performed according to instructions provided by the supplier (Progema). Rat GAPDH cDNA specific primer was used as control. There was a marked increase in mRNA level after 30 minutes of ischemia and 120 minutes of reperfusion (FIG. 5A). The increase in mRNA was sensitive to blockage of the $AT_1$ receptor, because pretreatment with losartan (L) reduced it almost entirely to the level of the control sample (C). The levels of the ribosomal marker L32 mRNA, used as control, remained unchanged.

EXAMPLE 4

This example demonstrates STAT activation during ischemia/reperfusion.

Figure 5B:
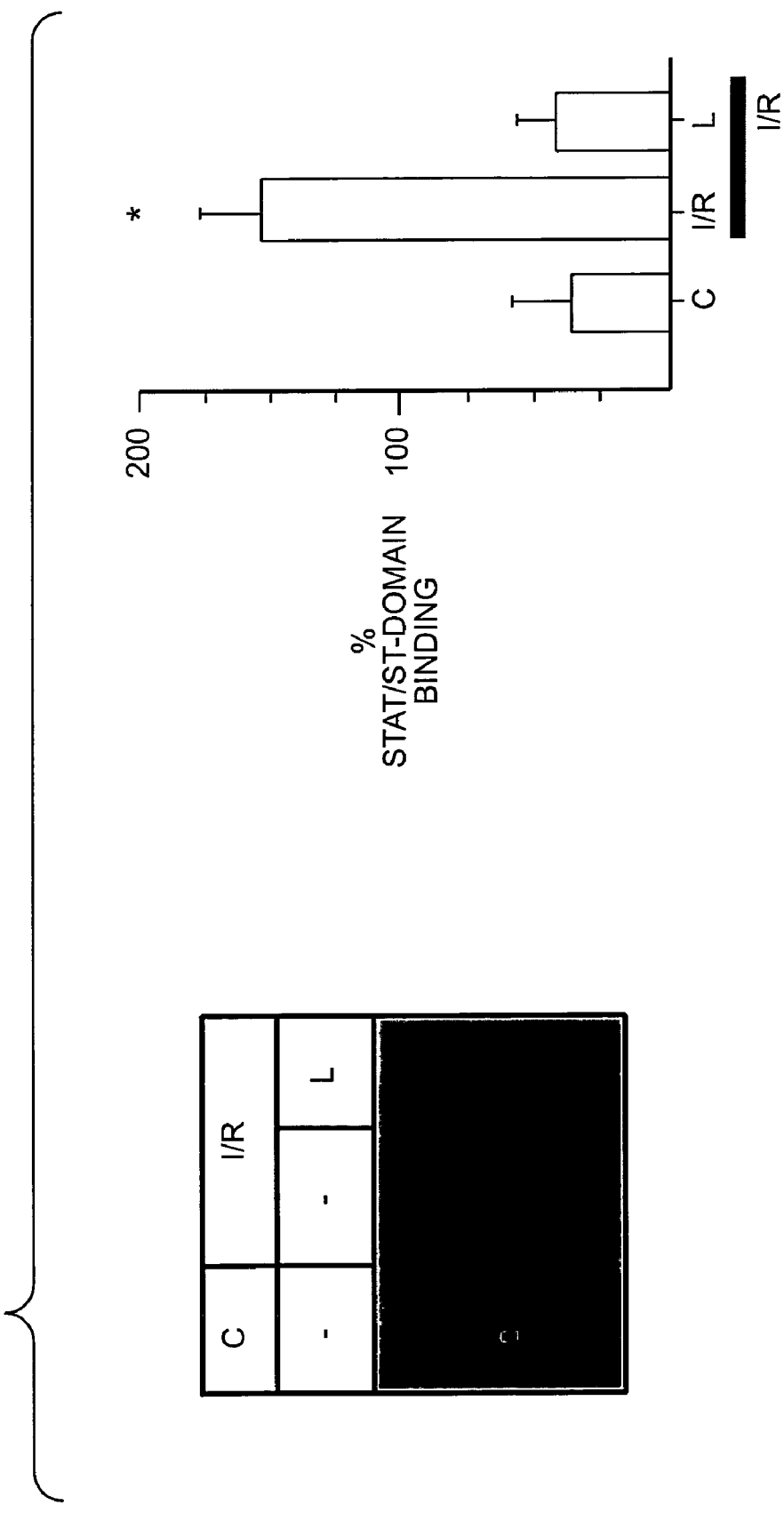

Nuclear extracts were examined in hearts subjected to global ischemia to determine whether there is enhanced STAT binding activity to the St domain of the angiotensinogen promoter. The nuclear heart extracts were examined by the electrophoretic gel mobility-shift assay that exployed the use of the chemically synthesized oligonucleotide sequence of the St domain. The St-domain DNA probe for protein binding was a double-stranded oligonucleotide containing the sequence 5'-GGGTtcCTGGAAGGG-3' SEQ. ID NO: 2, and complementary strand 5'-CCCTTCCAG-gaACCC-3' SEQ. ID NO: 3, respectively. These probes were end-labeled by polynucleotide kinase and $[\gamma\text{-}^{32}P]$ATP. Binding reaction mixture containing 0.5 ng of labeled DNA (1,000 cpm), 2 µg of poly(dI-C), and 1-12 µg of protein in buffer containing 20 mM Hepes, 3% glycerol, 1.5 mM $MgCl_2$, 1 mM DTT, 2 mM EDTA and 50 mM KCl, pH 7.5 was allowed to incubate at 4° C. for 30 min. The reactions were analyzed by electrophoresis on 8% polyacrylanide gel in 0.375× TBE (0.33 mM Tris borate, pH 8.7 and 1.0 mM EDTA). After electrophoresis, the gels were dried and subjected to autoradiography. There was a strong St-domain/STAT binding activity in the hearts subjected to 30 min. ischemia/120 min. reperfusion, which was almost entirely abolished in losartan-treated heart, suggesting that losartan (L) treatment during perfusion resulted in loss of the activated STAT participation in complex formation. (FIG. 5B). The activation of STATs and the consequent binding to the St-domain in the angiotensinogen promoter accounts for the increase in transcription of angiotensinogen mRNA. Thus, the loss of STAT/DNA interaction and the reduction in the angiotensinogen mRNA levels (see FIG. 5A) due to losartan treatment appear to be correlative.

Figure 5C:
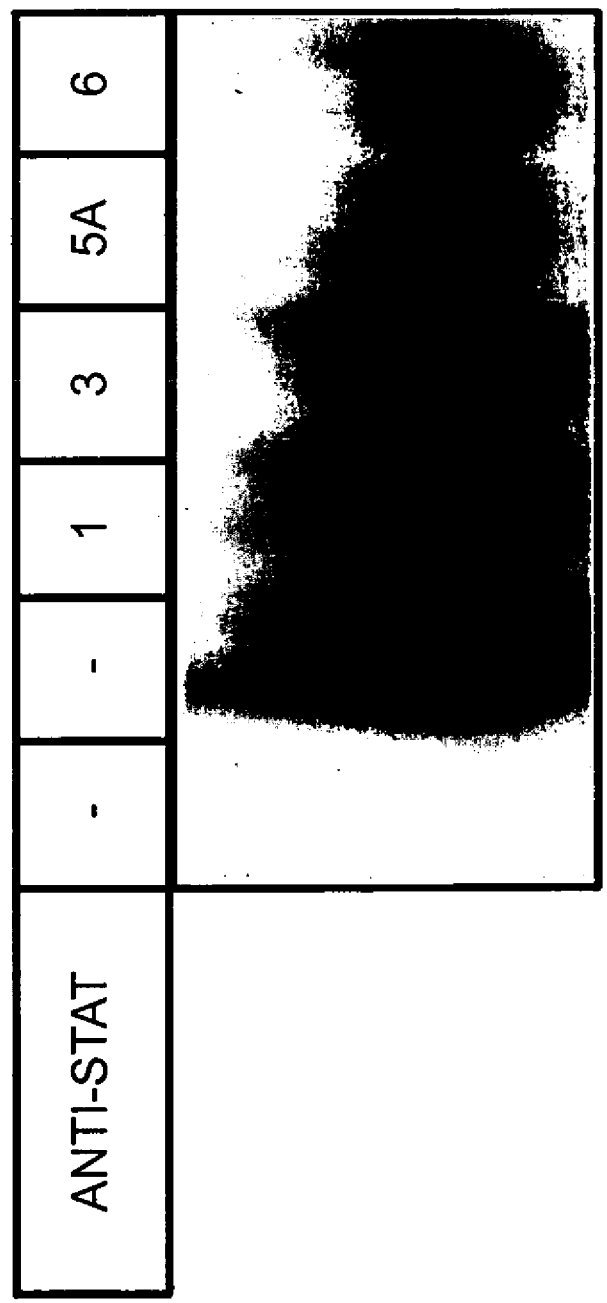

To identify the STAT proteins that were activated in the ischemic hearts, nuclear extracts were preincubated for 30 min with polyclonal antibodies against STAT1, STAT3, STAT5A, and STAT6 before adding the St-domain DNA labeled probe. Examination of the reaction by gel mobility-shift assay showed that STAT5A and STAT6 DNA complexes were prominently disrupted by antibodies against STAT5A and STAT6 (FIG. 5C). Therefore, STAT5A and STAT6 are activated in ischemic hearts.

EXAMPLE 5

This example demonstrates the effect of Jak2 inhibition on STAT/DNA binding and angiotensinogen mRNA.

Figure 6A:
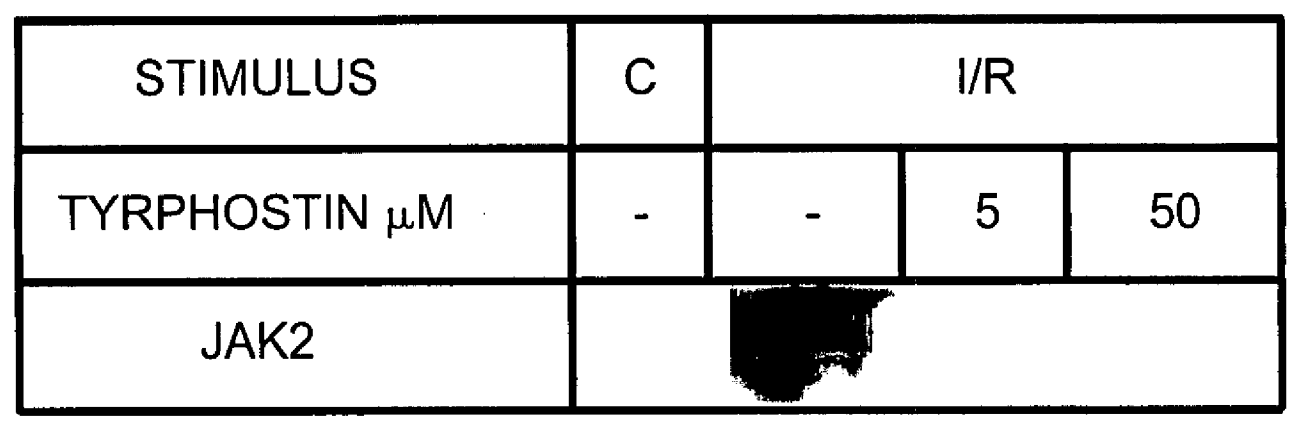

Rats were pretreated with 5 or 50 µmol/L of tyrphostin AG490 24 h prior to ischemia/reperfusion followed by chronic administration of tyrphostin AG490 during the process of ischemia/reperfusion. A phosphotyrosine assay was performed. Briefly, nuclear extracts from hearts subjected to ischemia/reperfusion in presence of absence of tyrphostin AG490 were immunoprecipitated with anti-phosphotyrosine antibodies (4G10). Fifty microliters of 50% protein A-agarose, prewashed in lysis buffer (Upstate Biotechnology) was then added and the mixture was incubated for 2 hr at 4° C. Each sample was washed with washing buffer containing 150 mM NaCl, 50 mM Tris-HCL (pH 7.4), 5 mM EDTA, 0.25% Triton X-100, 2 mM phenylmethylsulfonyl fluoride, aprotinin (0.2 unit/ml), 1 mM $Na_3VO_4$, and 1 mM NaF. Samples were eluted in 2× Laernmli's sample buffer. Proteins were separated on a 7.5% SDS/polyacrylamide gel and transferred to nitrocellulose membrane, Nitropure (Micron Separations, Westboro, Mass.). Blots were probed with polyclonal antibody against Jak2 and developed according to the chemiluminescence protocol. Administration of tyrphostin AG490 in perfusion medium was inhibitory at both 5 and 50 µmol/L for pliosphorylation of Jak2, which was activated readily in the ischemic heart in absence of the inhibitor (FIG. 6A).

Figure 6B:
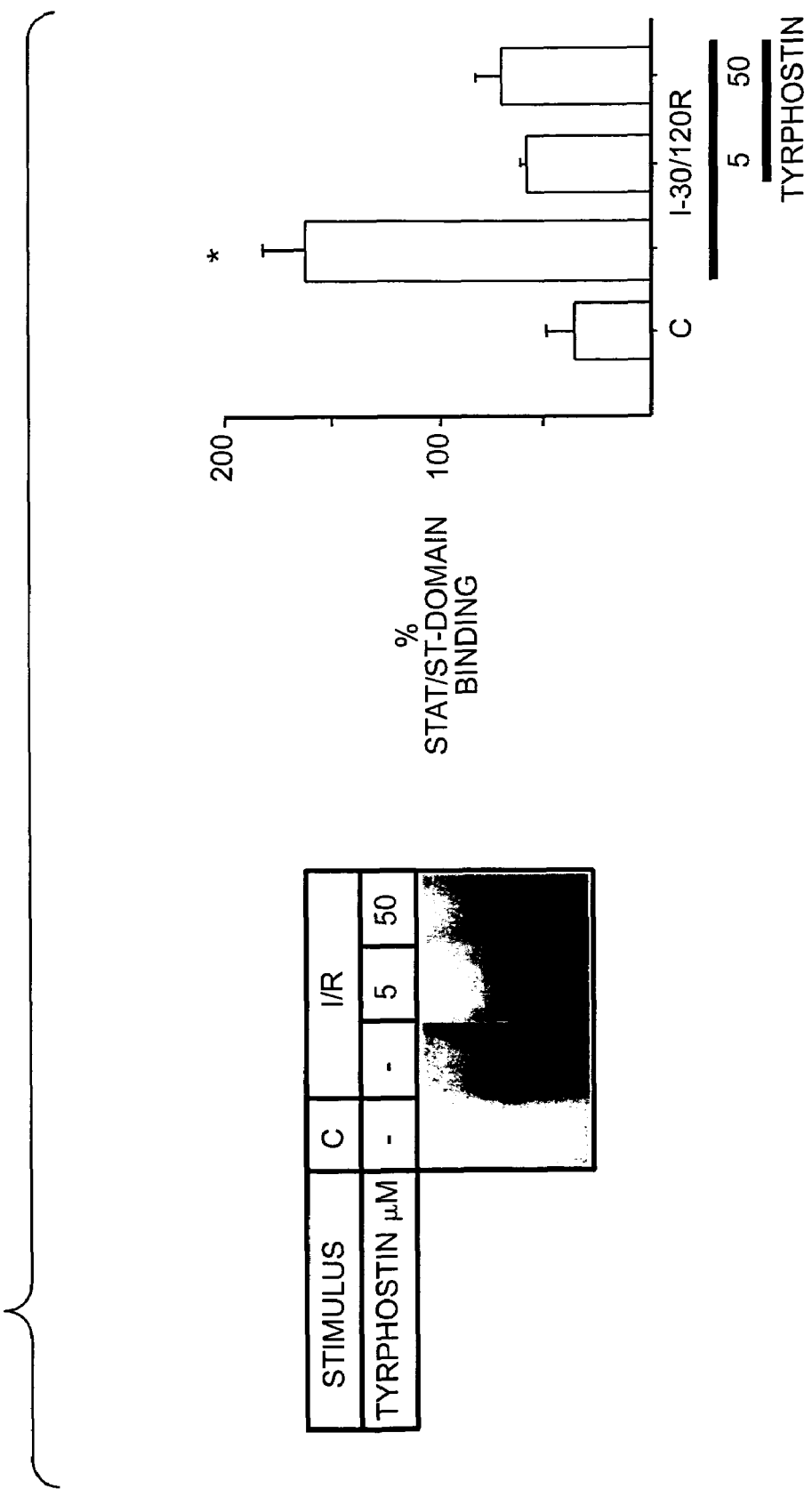
FIG. 6B: depicts reduction of St-domain/STAT binding activity by tyrphostin AG490 in hearts subjected to ischemia/reperfusion.
Figure 6C:
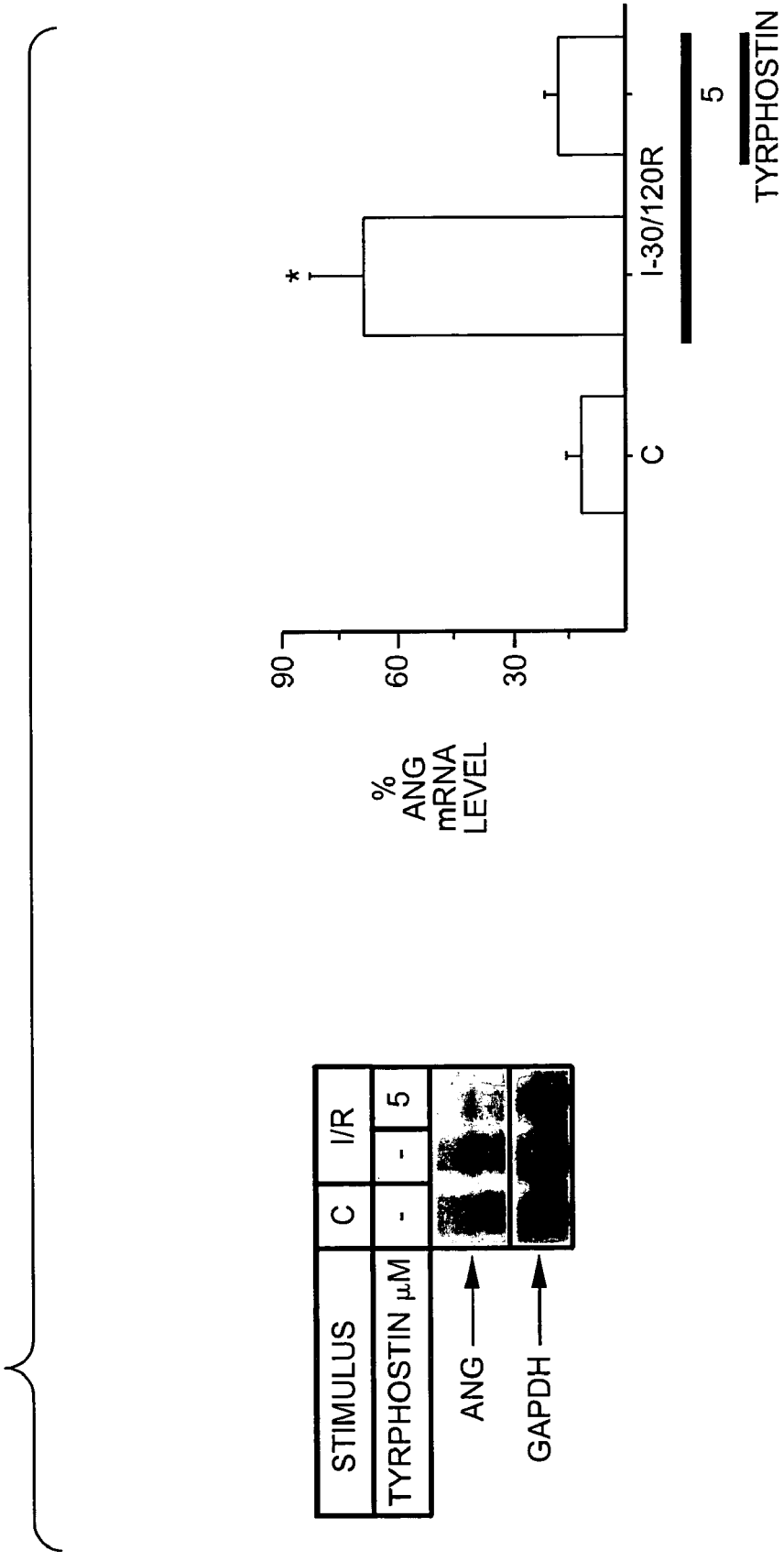
FIG. 6C: depicts inhibition of angiotensinogen mRNA by tyrphostin AG490 in hearts subjected to ischemia/reperfusion.

When extracts from the same hearts were examined by gel mobility-shift assay for DNA binding, there was a total loss of STAT/DNA complex formation in the tyrphostin AG490 treated hearts (FIG. 6B). Treatment with tyrphostin AG490 also inhibited the stimulation of the angiotensinogen mRNA level that was observed in the ischemic tissues in absence of the inhibitor (FIG. 6C). These results therefore strongly suggest that activation of the Jak/STAT pathway, increases in the STAT/angiotensinogen promoter binding activity, and the upregulation of angiotensinogen mRNA all are casually related.

EXAMPLE 6

This example demonstrates Jak2 is a potent activator of angiotensinogen gene expression.

Jak2 expression plasmid DNA was introduced via transfection into liver cells in culture along with the angiotensinogen (ANG)/luciferase reporter DNA. Transfections were performed using FUGENE (Boehringer Mannheim) to facilitate DNA uptake. A co-transfection assay with increasing concentration of plasmid pTELJAK2 (ng) that expresses a constitutively active Jak2 kinase and plasmid pANGLuc (1 µg) that carries the rat ANG promoter or plasmid pMAN-GLuc (1 µg) with a substitution mutation in the conserved St-domain were delivered in human hepatoma cell line HEPG2. After 48 hr, cells were collected and the luciferase activity of the reporter plasmids were evaluated using standard protocol (Luciferase assay TM-Promega).

Figure 7:
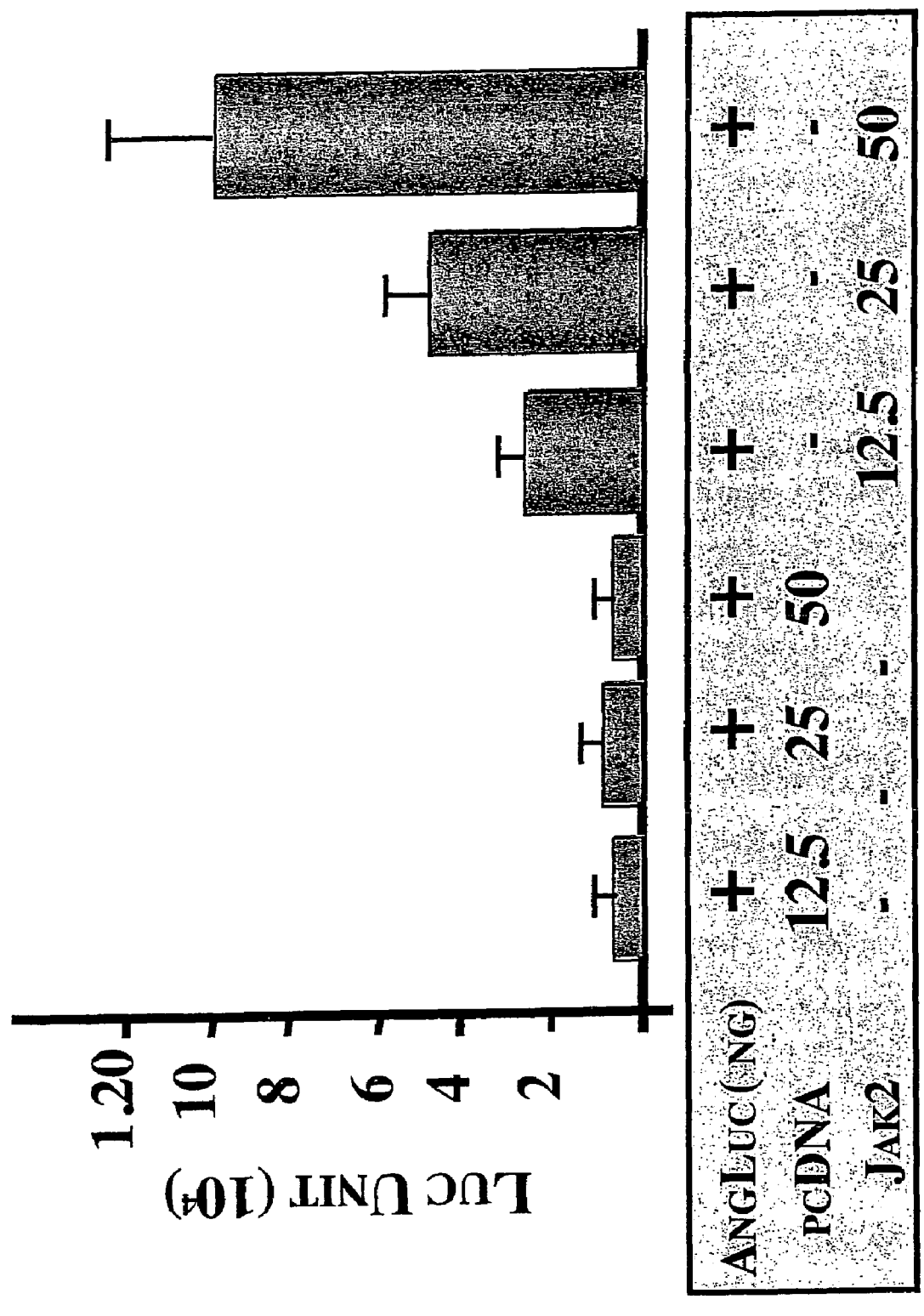
FIG. 7: depicts Jak2 as a potent activator of angiotensinogen gene expression.

Expression of angiotensinogen occurs in a concentration dependent manner (FIG. 7).

EXAMPLE 7

This example demonstrates attenuation of angiotensinogen mRNA expression in vivo by tyrphostin AG490.

Tyrphostin AG490 was administered to rats in vivo. A subcutaneous pump was surgically placed with a catheter extended intraperitoneally. Rats were daily treated with tyrphostin AG490 to achieve a 5 µM concentration systemically. After 10 days, the animals were euthanized using approved animal protocols and the liver collected to isolate RNA. The isolated RNA was used to perform a northern blot and the nitrocellulose membrane was probed with the rat angiotensinogen cDNA. Loading control was performed using GAPDH as probe.

Administration of tyrphostin AG490 abolished the expression of angiotensinogen gene product mRNA (FIG. 8).

EXAMPLE 8

This example demonstrates attenuation of hypertension by tyrphostin AG490.

Adult spontaneously hypertensive rats, which are genetically predisposed to hypertension, and normotensive rats were anesthetized with pentobarbital sodium (65 mg/kg ip) in preparation for surgery. Using aseptic rat surgical procedures, a groin incision was made to expose inferior epigastric vessels along with femoral vessel. Teflon arterial catheter (ID 0.029 mm) was inserted into the left femoral artery. The catheter was tunneled under the skin and exited at the nape of the rat's neck and connected to a 26 G needle capped on a port and flushed with 1:3 heparin saline.

The rats were housed individually after surgery, and allowed 48 hours to recover from the operation. Systolic and diastolic blood pressure were directly measured using the connection to the port placed in the rat's neck to a manual transducer.

Administration of 5 micromoles of tyrphostin AG490 to the hypertensive rats was effective in lowering blood pressure to normal levels (FIG. 9).

We claim:

1. A method for reducing hypertension in a mammal at risk for developing damage due to said hypertension comprising administering to said mammal an effective amount of a selective Jak2 inhibitor.

2. A method as set forth in claim 1 wherein said Jak2 inhibitor is a tyrphostin.

3. A method as set forth in claim 2 wherein said tyrphostin is Tyrphostin AG490.

4. A method as set forth in claim 1 wherein said mammal is human.

5. A method as set forth in claim 1 wherein said administration of the Jak2 inhibitor is systemic.

6. A method as set forth in claim 1 wherein said composition is administered before damage from said hypertension occurs.

7. A method as set forth in claim 1 wherein said effective amount produces a blood serum level between about 0.05 µM to about 10 µM.

8. A method as set forth in claim 7 wherein said effective amount produces a blood serum level preferably between about 1 µM to about 5 µM.

9. A method for reducing heart failure in a mammal at risk for developing damage due to said heart failure comprising administering to said mammal an effective amount of a selective Jak 2 inhibitor.

10. A method as set forth in claim 9 wherein said Jak2 inhibitor is a tyrphostin.

11. A method as set forth in claim 10 wherein said tyrphostin is Tyrphostin AG490.

12. A method as set forth in claim 9 wherein said mammal is human.

13. A method as set forth in claim 9 wherein said composition is administered before said heart failure occurs.

14. A method as set forth in claim 9, wherein said composition is administered after said heart failure occurs to inhibit further damage.

15. A method as set forth in claim 9 wherein said administration of the Jak2 inhibitor is systemic.

16. A method as set forth in claim 9 wherein said effective amount is an amount that produces a blood serum level between about 0.05 µM to about 10 µM.

17. A method as set forth in claim 16 wherein said effective amount is an amount that produces a blood serum level preferably between about 1 µM to about 5 µM.

* * * * *